United States Patent
Trollsas

(10) Patent No.: US 10,155,881 B2
(45) Date of Patent: *Dec. 18, 2018

(54) SUBSTITUTED POLYCAPROLACTONE FOR COATING

(75) Inventor: Mikael O. Trollsas, San Jose, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 1007 days.

This patent is subject to a terminal disclaimer.

(21) Appl. No.: 11/809,059

(22) Filed: May 30, 2007

(65) Prior Publication Data

US 2008/0299164 A1  Dec. 4, 2008

(51) Int. Cl.
  *C09D 167/04* (2006.01)
  *A61L 31/10* (2006.01)
  *A61L 31/16* (2006.01)

(52) U.S. Cl.
  CPC ............ *C09D 167/04* (2013.01); *A61L 31/10* (2013.01); *A61L 31/16* (2013.01); *A61L 2300/20* (2013.01); *A61L 2300/416* (2013.01)

(58) Field of Classification Search
  None
  See application file for complete search history.

(56) References Cited

U.S. PATENT DOCUMENTS

| | | |
|---|---|---|
| 5,272,012 A | 12/1993 | Opolski |
| 5,702,754 A | 12/1997 | Zhong |
| 5,869,127 A | 2/1999 | Zhong |
| 5,997,517 A | 12/1999 | Whitbourne |
| 6,001,117 A | 12/1999 | Huxel et al. |
| 6,099,563 A | 8/2000 | Zhong |
| 6,110,483 A | 8/2000 | Whitbourne et al. |
| 6,179,817 B1 | 1/2001 | Zhong |
| 6,197,051 B1 | 3/2001 | Zhong |
| 6,274,164 B1 | 8/2001 | Novich |
| 6,306,176 B1 | 10/2001 | Whitbourne |
| 6,494,862 B1 | 12/2002 | Ray et al. |
| 6,503,538 B1 | 1/2003 | Chu et al. |
| 6,544,223 B1 | 4/2003 | Kokish |
| 6,544,543 B1 | 4/2003 | Buchk et al. |
| 6,656,216 B1 | 12/2003 | Hossainy |
| 6,656,506 B1 | 12/2003 | Wu et al. |
| 6,663,662 B2 | 12/2003 | Pacetti et al. |
| 6,663,880 B1 | 12/2003 | Roorda et al. |
| 6,673,154 B1 | 1/2004 | Pacetti et al. |
| 6,703,040 B2 | 3/2004 | Katsarava |
| 6,712,845 B2 | 3/2004 | Hossainy |
| 6,743,462 B1 | 6/2004 | Pacetti |
| 6,753,071 B1 | 6/2004 | Pacetti |
| 6,758,859 B1 | 7/2004 | Kenny |
| 6,790,228 B2 | 9/2004 | Hossainy |
| 6,818,063 B1 | 11/2004 | Kerrigan |
| 6,824,559 B2 | 11/2004 | Michal |
| 6,926,919 B1 | 8/2005 | Hossainy et al. |
| 6,972,054 B2 | 12/2005 | Kerrigan |
| 7,005,137 B1 | 2/2006 | Hossainy et al. |
| 7,022,334 B1 | 4/2006 | Ding |
| 7,056,591 B1 | 6/2006 | Pacetti et al. |
| 7,060,093 B2 | 6/2006 | Dang |
| 7,074,276 B1 | 7/2006 | Sciver et al. |
| 7,115,300 B1 | 10/2006 | Hossainy et al. |
| 7,135,038 B1 | 11/2006 | Limon |
| 7,166,680 B2 | 1/2007 | Desnoyer |
| 7,169,178 B1 | 1/2007 | Santos et al. |
| 7,175,874 B1 | 2/2007 | Pacetti |
| 7,201,935 B1 | 4/2007 | Claude et al. |
| 7,202,325 B2 | 4/2007 | Hossainy |
| 7,217,426 B1 | 5/2007 | Hossainy |
| 7,232,490 B1 | 6/2007 | Hossainy |
| 7,232,573 B1 | 6/2007 | Ding |
| 7,244,443 B2 | 7/2007 | Pacetti |
| 7,247,313 B2 | 7/2007 | Roorda et al. |
| 7,255,891 B1 | 8/2007 | Pacetti |
| 7,261,946 B2 | 8/2007 | Claude |
| 7,288,609 B1 | 10/2007 | Pacetti |
| 7,294,329 B1 | 11/2007 | Ding |
| 7,311,980 B1 | 12/2007 | Hossainy et al. |
| 7,323,209 B1 | 1/2008 | Esbeck et al. |
| 7,329,413 B1 | 2/2008 | Pacetti |
| 7,335,265 B1 | 2/2008 | Hossainy |
| 7,335,391 B1 | 2/2008 | Pacetti |
| 7,341,630 B1 | 3/2008 | Pacetti |
| 8,057,813 B2 | 11/2011 | Toner et al. |
| 2001/0007083 A1 | 7/2001 | Roorda |
| 2003/0073961 A1 | 4/2003 | Happ |
| 2003/0104028 A1 | 6/2003 | Hossainy et al. |
| 2003/0105518 A1 | 6/2003 | Dutta |
| 2003/0158517 A1 | 8/2003 | Kokish |
| 2003/0082368 A1 | 10/2003 | Hossainy |
| 2004/0039441 A1* | 2/2004 | Rowland et al. ............ 623/1.42 |
| 2004/0047980 A1 | 3/2004 | Pacetti |
| 2004/0052858 A1 | 3/2004 | Wu et al. |
| 2004/0054104 A1 | 3/2004 | Pacetti |
| 2004/0060508 A1 | 4/2004 | Pacetti |
| 2004/0062853 A1 | 4/2004 | Pacetti et al. |
| 2004/0063805 A1 | 4/2004 | Hossainy |
| 2004/0071861 A1 | 4/2004 | Mandrusov |
| 2004/0072922 A1 | 4/2004 | Hossainy |
| 2004/0073298 A1 | 4/2004 | Hossainy |
| 2004/0086542 A1 | 5/2004 | Hossainy |
| 2004/0142015 A1 | 7/2004 | Hossainy et al. |
| 2004/0162609 A1 | 8/2004 | Hossainy et al. |
| 2004/0180132 A1 | 9/2004 | Pacetti |
| 2004/0182312 A1 | 9/2004 | Pacetti et al. |
| 2004/0191405 A1 | 9/2004 | Kerrigan |
| 2004/0253203 A1 | 12/2004 | Hossainy |
| 2005/0021127 A1 | 1/2005 | Kawula |

(Continued)

FOREIGN PATENT DOCUMENTS

| | | |
|---|---|---|
| WO | WO 2005/000939 | 1/2005 |
| WO | WO 2007/024481 | 3/2007 |

OTHER PUBLICATIONS

Trollsas et al, 1999. Highly functional branched block copolymers: Design, synthesis and morphology. Macromolecules, v. 32:4917-4924.*

(Continued)

*Primary Examiner* — Tigabu Kassa
(74) *Attorney, Agent, or Firm* — Squire Patton Boggs (US) LLP

(57) ABSTRACT

A coating formed of a substituted polycaprolactone and method of making and using the same are disclosed.

9 Claims, 2 Drawing Sheets

(56) References Cited

U.S. PATENT DOCUMENTS

| | | | |
|---|---|---|---|
| 2005/0025799 A1 | 2/2005 | Hossainy | |
| 2005/0074544 A1 | 4/2005 | Pacetti et al. | |
| 2005/0095267 A1* | 5/2005 | Campbell et al. | 424/425 |
| 2005/0112170 A1 | 5/2005 | Hossainy et al. | |
| 2005/0112171 A1 | 5/2005 | Tang et al. | |
| 2005/0118344 A1 | 6/2005 | Pacetti | |
| 2005/0137381 A1 | 6/2005 | Pacetti | |
| 2005/0147647 A1 | 7/2005 | Galuser et al. | |
| 2005/0169957 A1 | 8/2005 | Hossainy | |
| 2005/0175666 A1 | 8/2005 | Ding | |
| 2005/0208091 A1 | 9/2005 | Pacetti | |
| 2005/0214339 A1 | 9/2005 | Tang et al. | |
| 2005/0226991 A1 | 10/2005 | Hossainy et al. | |
| 2005/0233062 A1* | 10/2005 | Hossainy et al. | 427/2.1 |
| 2005/0244363 A1 | 11/2005 | Hossainy et al. | |
| 2005/0265960 A1 | 12/2005 | Pacetti et al. | |
| 2005/0271700 A1 | 12/2005 | Desnoyer et al. | |
| 2005/0287184 A1 | 12/2005 | Hossainy et al. | |
| 2006/0002968 A1 | 1/2006 | Stewart et al. | |
| 2006/0034888 A1 | 2/2006 | Pacetti et al. | |
| 2006/0043650 A1 | 3/2006 | Hossainy et al. | |
| 2006/0062824 A1 | 3/2006 | Pacetti et al. | |
| 2006/0089485 A1 | 4/2006 | Desnoyer et al. | |
| 2006/0095122 A1 | 5/2006 | Pacetti | |
| 2006/0115449 A1 | 6/2006 | Pacetti | |
| 2006/0134165 A1 | 6/2006 | Pacetti | |
| 2006/0136048 A1 | 6/2006 | Pacetti et al. | |
| 2007/0032853 A1 | 2/2007 | Hossainy et al. | |
| 2007/0190104 A1* | 8/2007 | Kamath et al. | 424/423 |
| 2007/0264307 A1* | 11/2007 | Chen et al. | 424/426 |

OTHER PUBLICATIONS

Malmstrom et al, 1996. The effect of terminal alkyl chains on hyperbranched polyesters based on 2,2-bis(hydroxymethyl)propionic acid. Macromol. Chem., vol. 197:3199-3207.*

Grube and Buellesfeld, 2004. Rapamycin analogs for stent-based local drug delivery. Herz, vol. 29:162-166.*

Merriam-Webster's Online Dictionary definition of topcoat and overcoat.*

U.S. Appl. No. 09/406,473, Pacetti, filed Sep. 27, 1999.
U.S. Appl. No. 09/894,293, Roorda et al., filed Jun. 27, 2001.
U.S. Appl. No. 09/966,786, Hossainy, filed Sep. 27, 2001.
U.S. Appl. No. 09/967,632, Pacetti, filed Sep. 28, 2001.
U.S. Appl. No. 10/040,538, Pacetti et al., filed Dec. 28, 2001.
U.S. Appl. No. 10/104,772, Dutta, filed Mar. 20, 2002.
U.S. Appl. No. 10/177,154, Hossainy et al., filed Jun. 21, 2002.
U.S. Appl. No. 10/177,942, Michal et al., filed Jun. 21, 2002
U.S. Appl. No. 10/246,883, Taylor, filed Sep. 18, 2002
U.S. Appl. No. 10/260,182, Hossainy, filed Sep. 27, 2002
U.S. Appl. No. 10/271,851, Roorda, filed Oct. 15, 2002
U.S. Appl. No. 10/286,058, Pacetti et al., filed Oct. 31, 2002
U.S. Appl. No. 10/316,739, Zhang et al., filed Dec. 10, 2002
U.S. Appl. No. 10/327,371, Lin et al., filed Dec. 19, 2002.
U.S. Appl. No. 10/330,412, Hossainy et al., filed Dec. 27, 2002.
U.S. Appl. No. 10/375,496, Esbeck, filed Feb. 26, 2003.
U.S. Appl. No. 10/376,027, Kokish et al., filed Feb. 26, 2003.
U.S. Appl. No. 10/376,348, Ding et al., filed Feb. 26, 2003.
U.S. Appl. No. 10/428,691, Pacetti, filed May 1, 2003.
U.S. Appl. No. 10/606,711, Pacetti, filed Jun. 26, 2003.
U.S. Appl. No. 10/631,116, Dehnad, filed Jul. 31, 2003.
U.S. Appl. No. 10/705,546, Kwok et al., filed Nov. 10, 2003.
U.S. Appl. No. 10/729,728, Pacetti, filed Dec. 5, 2003.
U.S. Appl. No. 10/835,229, Prabhu et al., filed Apr. 28, 2004.
U.S. Appl. No. 10/851,411, Chen, filed May 20, 2004.
U.S. Appl. No. 10/853,924, Pathak, filed May 25, 2004.
U.S. Appl. No. 10/877,419, Pacetti, filed Jun. 25, 2004.
U.S. Appl. No. 10/883,242, Roorda et al., filed Jun. 30, 2004.
U.S. Appl. No. 10/909,795, Ding et al., filed Jul. 30, 2004.
U.S. Appl. No. 10/913,607, Pacetti et al., filed Aug. 5, 2004.
U.S. Appl. No. 10/932,364, Foreman et al., filed Aug. 31, 2004.
U.S. Appl. No. 10/976,550, Pacetti et al., filed Oct. 29, 2004.

Atthoff et al., "Dendrimer-Like Star Polymers", Polymer Preprints vol. 39, No. 2, pp. 76-77 (1998).

Hedrick et al., "Dendrimer-Like Star Block and Amphiphilic Copolymers by Combination of Ring Opening and Atom Transfer Radical Polymerization", Macromolecules 31, pp. 8691-8705 (1998).

Trollsås et al., "Highly Functional Branched and Dendri-Graft Aliphatic Polyesters through Ring Opening Polymerization", Macromolecules 31, pp. 2756-2763 (1998).

Trollsås et al., "Hyperbranched Poly($\varepsilon$-caprolactone) Derived from Intrinsically Branched $AB_2$ Macromonomers", Macromolecules 31, pp. 4390-4395 (1998).

Trollsås et al., "Highly Branched Block Copolymers: Design, Synthesis, and Morphology", Macromolecules 32, pp. 4917-4924 (1999).

Trollsås et al., "Dendrimer-like Star Polymers", J. Am. Chem. Soc. 120, pp. 4644-4651 (1998).

Trollsås et al., "Layered Dendritic Block Copolymers", Angew. Chem. Int. Ed. 37, No. 22 pp. 3132-3136 (1998).

International Search Report for PCT/US2008/062790, dated Aug. 6, 2008, 14 pgs.

Ihre et al., "Double-Stage Convergent Approach for the Synthesis of Functionalized Dendritic Aliphatic Polyesters Based on 2.2-Bis(hydroxymethyl) propionic Acid", Macromolecules 31, pp. 4061-4068 (1998).

Trollsas et al., "Versatile and Controlled Synthesis of Star and Branched Macromolecules by Dentritic Initiation", Macromolecules 30, pp. 8508-8511 (1997).

European Search Report for appl. 08755087.7, dated Apr. 9, 2010, 5 pgs.

Trollsas et al., "Hyperbranched Poly(Epsilon-Caprolactone)s", Macromolecules, ACS, Washington, DC, vol. 31, No. 11, pp. 3439-3445 (1998).

Ikeda et al., "Patient-Specific Blood Vessel Scaffold for Regenerative Medicine" *Proceedings of 2007 IEEE International Conference on Robotics and Automation,* vol. 4, pp. 1912-1917 (2007).

Hietala et al. "Platelet responses and coagulation activation on polylactide and heparin-polycaprolactone-L-lactide -coated polylactide stent struts" *Journal of Biomedical Materials Research Part A,* vol. 67A, iss. 3, pp. 785-791 (2003).

* cited by examiner

Scheme 2

SUBSTITUTED POLYCAPROLACTONE FOR COATING

FIELD OF THE INVENTION

This invention generally relates to a substituted polycaprolactone for biomedical applications such as coating a stent.

DESCRIPTION OF THE BACKGROUND

Blood vessel occlusions are commonly treated by mechanically enhancing blood flow in the affected vessels, such as by employing a stent. Stents are used not only for mechanical intervention but also as vehicles for providing biological therapy. To effect a controlled delivery of an active agent in stent medication, the stent can be coated with a biocompatible polymeric coating. The biocompatible polymeric coating can function either as a permeable layer or a carrier to allow a controlled delivery of the agent.

Although stents work well mechanically, the chronic issues of restenosis and, to a lesser extent, stent thrombosis remain. Pharmacological therapy in the form of a drug delivery stent appears to be a feasible means to tackle these issues. Polymeric coatings placed onto the stent serve to act both as the drug reservoir and to control the release of the drug. One of the commercially available polymer-coated products is a stent manufactured by Boston Scientific. For example, U.S. Pat. Nos. 5,869,127; 6,099,563; 6,179,817; and 6,197,051, assigned to Boston Scientific Corporation, describe various compositions for coating medical devices. These compositions provide to stents described therein an enhanced biocompatibility and may optionally include a bioactive agent. U.S. Pat. No. 6,231,590 to Scimed Life Systems, Inc., describes a coating composition, which includes a bioactive agent, a collagenous material, or a collagenous coating optionally containing or coated with other bioactive agents.

The nature of the coating polymers plays an important role in defining the surface properties of a coating. For example, coating integrity depends largely on the nature of the polymer forming the coating. Intrinsic polymer properties such as morphology, Tg, elasticity, and hydrophilicity all affect important characteristics and as an example a high $T_g$ or highly crystalline coating material may introduce brittle fractures in the high strain areas of the stent pattern.

Therefore, there is a need for polymeric materials that can be tailored to meet need of a coating on a medical device.

The polymer and methods of making the polymer disclosed herein address the above-described problems.

SUMMARY OF THE INVENTION

Provided herein is a coating or a delivery vehicle including a substituted polycaprolactone. Substituted polycaprolactone is usually amorphous and the pendent groups can help to provide controlled release of drug from the coating or delivery vehicle. In some embodiments, the delivery vehicle can comprise microparticles or nanoparticles.

In some embodiments, the coating or delivery vehicle can include a bioactive agent. The bioactive agent can be any diagnostic agent, therapeutic agent, or preventive agent. Some examples of such bioactive agents include, but are not limited to, paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), γ-hiridun, clobetasol, mometasone, pimecrolimus, imatinib mesylate, or midostaurin, or prodrugs, co-drugs, or combinations of these. In some embodiments, the hydrophilic bioactive agent can be a peptide (e.g., RGD, cRGD or mimetics thereof) or a drug carrying a charge.

A medical device having a coating or a delivery vehicle described herein can be used to treat, prevent, or ameliorate a medical condition such as atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, urethra obstruction, tumor obstruction, and combinations thereof.

DETAILED DESCRIPTION

Figure 1:
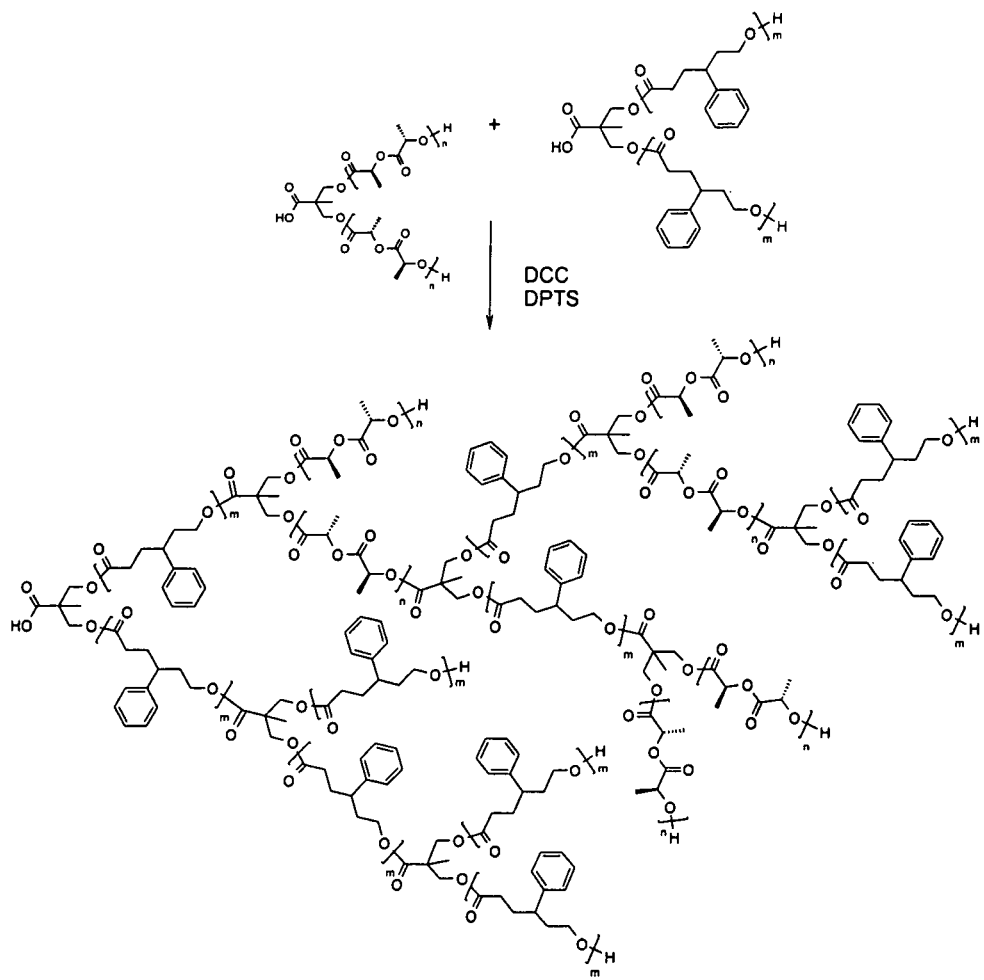
FIG. 1 shows the preparation of a substituted polycaprolactone block copolymer of an embodiment of the present invention.

Provided herein is a coating or a delivery vehicle including a substituted polycaprolactone. Substituted polycaprolactone is usually amorphous and the pendent groups can help to provide controlled release of drug from the coating or delivery vehicle. In some embodiments, the delivery vehicle can comprise microparticles or nanoparticles.

In some embodiments, the coating or delivery vehicle can include a bioactive agent. The bioactive agent can be any diagnostic agent, therapeutic agent, or preventive agent. Some examples of such bioactive agents include, but are not limited to, paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), γ-hiridun, clobetasol, mometasone, pimecrolimus, imatinib mesylate, or midostaurin, or prodrugs, co-drugs, or combinations of these. In some embodiments, the hydrophilic bioactive agent can be a peptide (e.g., RGD, cRGD or mimetics thereof) or a drug carrying a charge.

A medical device having a coating or a delivery vehicle described herein can be used to treat, prevent, or ameliorate a medical condition such as atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, urethra obstruction, tumor obstruction, and combinations thereof.

Substituted Polycaprolactone

The substituted polycaprolactone polymer useful for forming a coating or a delivery vehicle described herein can have be any substituted polycaprolactone polymer, which can be homopolymer or copolymer. The copolymer can be random, alternating, or block copolymer.

In some embodiments, the substituted polycaprolactone polymer can comprise a general structure of Formula I:

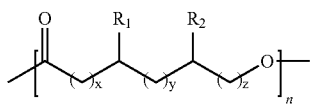

Formula I where:

x, y, and z are independent integers having values ranging from 0-20, e.g., 0, 1, 2, 3, 4, 5, 6, 7, 8, 9, 10, 11, 12, 13, 14, 15, 16, 17, 18, 19 and 20;

n is an integer ranging from 1 to about 100,000, e.g., from about 5 to about 50,000, from about 10 to about 10,000, from about 100 to about 5,000, from about 500 to about 2,000 or about 1,000;

$R_1$ and $R_2$ are independently hydrogen or any of C1-C20 substituents. Some examples of $R_1$ and $R_2$ can be straight-chained or branch-chained alkyl groups, such as methyl, ethyl, propyl, isopropyl, n-butyl, or iso-butyl; cyclo alkyl or substituted cyclo alkyl groups, such as cyclohexyl or 1,4-dimethyl cyclohexyl; straight-chained or branch-chained alkoxy groups, such as methoxy, ethoxy, butoxy, or iso-butoxy; phenyl, phenoxy, aryl, aryloxy, ketones, esters, olefins, ethers, unsaturations, thioethers, thioesters, amides, amines, thiols/mercaptans, phenols, other alcohols. In some embodiments, $R_1$ and $R_2$ can independently include one or more

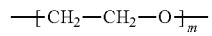

group where m is a positive integer ranging from 1 to 100, e.g., 2, 3, 4, 5, 6, 7, 8, 9, 10, 11, 12, 13, 14, 15, 16, 17, 18, 19, or 20. In some embodiments, $R_1$ and $R_2$ can independently include a heteroatom substituent(s) such as oxygen, halo atom(s) (F, Cl, Br or I), S, and N. In some embodiments, $R_1$ and $R_2$ can independently include one or more carbo substituent such as methyl, ethyl, or phenyl;

$R_1$ and $R_2$ cannot both be hydrogen; and $R_1$, $R_2$, X, y, and z are selected such that the structure of Formula I is not a polylactic acid (PLA), polyglycolic acid (PGA), polyhydroxybutyric acid (PBH), polyhydroxyvaleric acid, valerolactone, caprolactone, dioxanone or a copolymer thereof.

In some embodiments, the substituted polycaprolactone polymer can comprise a general structure of Formula II:

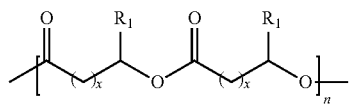

Formula II where:

x are independent integers having values ranging from 0-20, e.g., 0, 1, 2, 3, 4, 5, 6, 7, 8, 9, 10, 11, 12, 13, 14, 15, 16, 17, 18, 19 and 20;

n is an integer ranging from 1 to about 100,000, e.g., from about 5 to about 50,000, from about 10 to about 10,000, from about 100 to about 5,000, from about 500 to about 2,000 or about 1,000;

the two $R_1$ groups are independently hydrogen or any of C1-C20 substituents. Some examples of $R_1$ can be straight-chained or branch-chained alkyl groups, such as methyl, ethyl, propyl, isopropyl, n-butyl, or iso-butyl; cyclo alkyl or substituted cyclo alkyl groups, such as cyclohexyl or 1,4-dimethyl cyclohexyl; straight-chained or branch-chained alkoxy groups, such as methoxy, ethoxy, butoxy, or iso-butoxy; phenyl, phenoxy, aryl, or aryloxy, ketones, esters, olefins, ethers, unsaturations, thioethers, thioesters, amides, amines, thiols/mercaptans, phenols, other alcohols. In some embodiments, In some embodiments, the two $R_1$ groups can independently include one or more

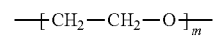

group where m is a positive integer ranging from 1 to 100, e.g., 2, 3, 4, 5, 6, 7, 8, 9, 10, 11, 12, 13, 14, 15, 16, 17, 18, 19, or 20. In some embodiments, the $R_1$ groups can independently include a heteroatom substituent(s) such as oxygen, halo atom(s) (F, Cl, Br or I), S, and N. In some embodiments, the $R_1$ groups can independently include one or more carbo substituent such as methyl, ethyl, or phenyl;

the two $R_1$ cannot both be hydrogen; and the two $R_1$ groups and x are selected such that the polymer comprising the structure of Formula II is not a polylactic acid (PLA), polyglycolic acid (PGA), polyhydroxybutyric acid (PBH), polyhydroxyvaleric acid, valerolactone, caprolactone, dioxanone or a copolymer thereof.

In some embodiments, the $R_1$, $R_2$, x, y, and z in Formulae I or II of the substituted polycaprolactone described above are selected such that the structure of Formulae I or II are not simultaneously a polylactic acid (PLA), polyglycolic acid (PGA), polyhydroxybutyric acid (PBH), polyhydroxyvaleric acid, valerolactone, caprolactone, dioxanone or a copolymer thereof.

Some examples of the substituted polycaprolactone comprising the structure of Formulae I or II are listed in Table 1 below.

TABLE 1

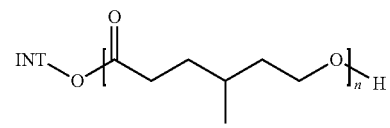

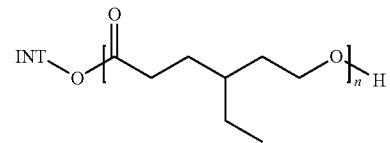

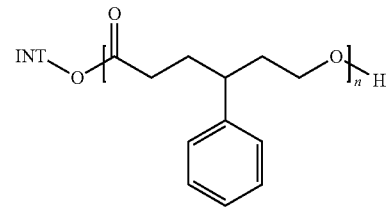

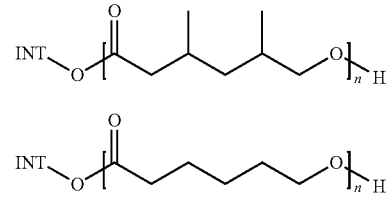

TABLE 1-continued

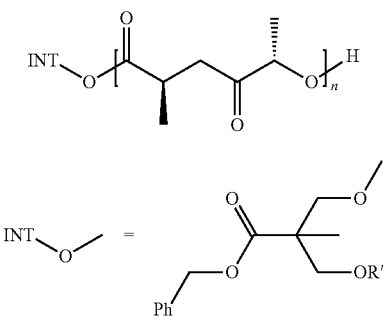

In Table 1, n is an integer ranging from 1 to about 100,000, e.g., from about 5 to about 50,000, from about 10 to about 10,000, from about 100 to about 5,000, from about 500 to about 2,000 or about 1,000; and R' is hydrogen or an organic group such as a protective group.

In some embodiments, the substituted polycaprolactone can be a block copolymer. Such block copolymer can include two or more blocks of substituted polycaprolactone blocks. Some examples of these substituted polycaprolactone blocks can have a structure of Formulae I or II, defined above. Some examples of a block copolymer of substituted polycaprolactone are shown in Table 2, below. These block-copolymers could also be synthesized in a more traditional sequential fashion without the use of bis-MPA as an initiator resulting in a linear block copolymer.

TABLE 2

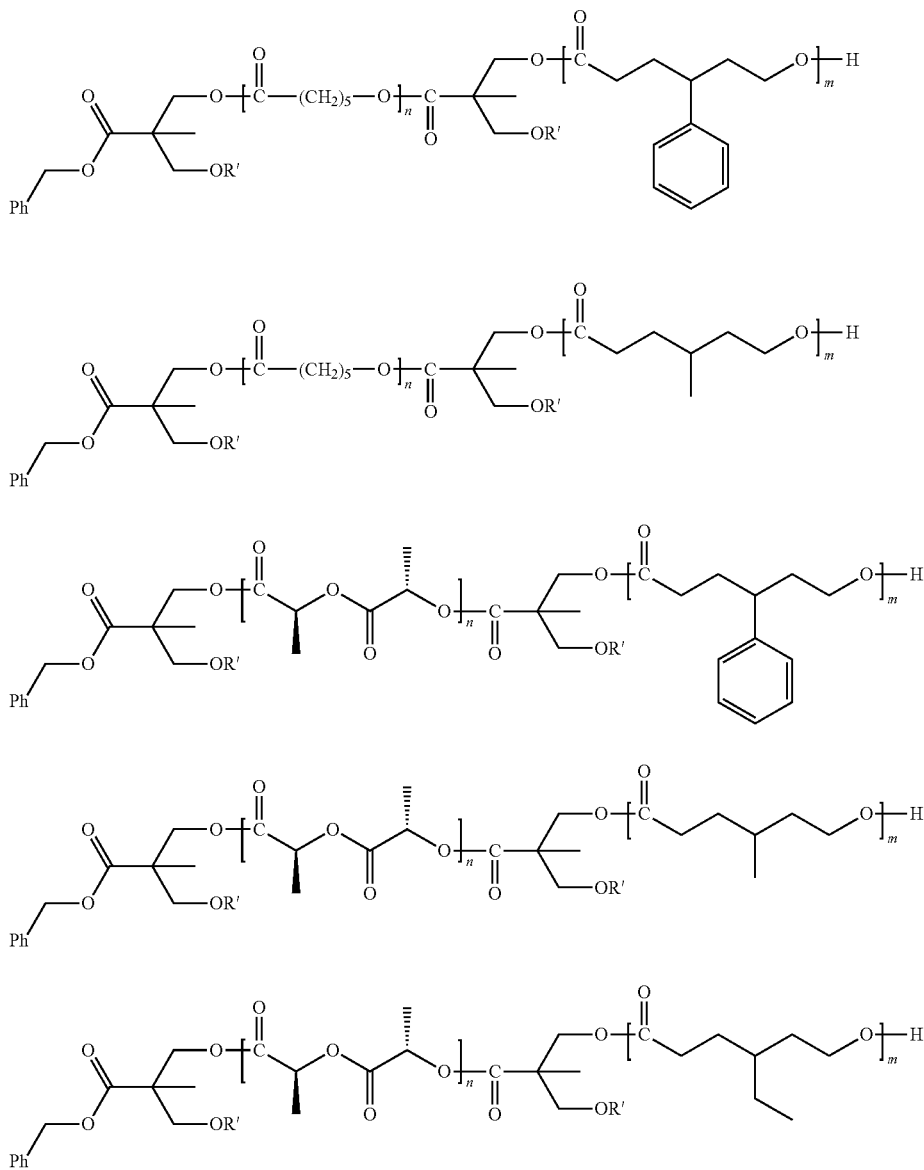

TABLE 2-continued

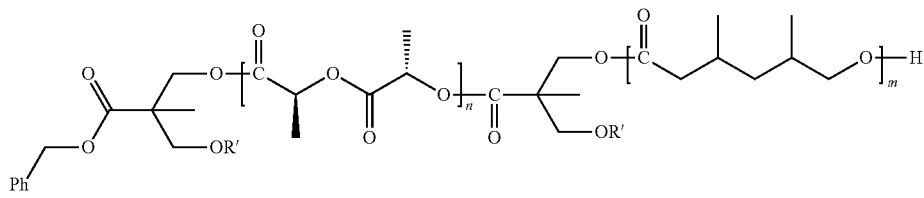

In Table 2, n and m are independent integers ranging from 1 to about 100,000, e.g., from about 5 to about 50,000, from about 10 to about 10,000, from about 100 to about 5,000, from about 500 to about 2,000 or about 1,000; and R' is hydrogen or an organic group such as a protective group.

Figure 2:
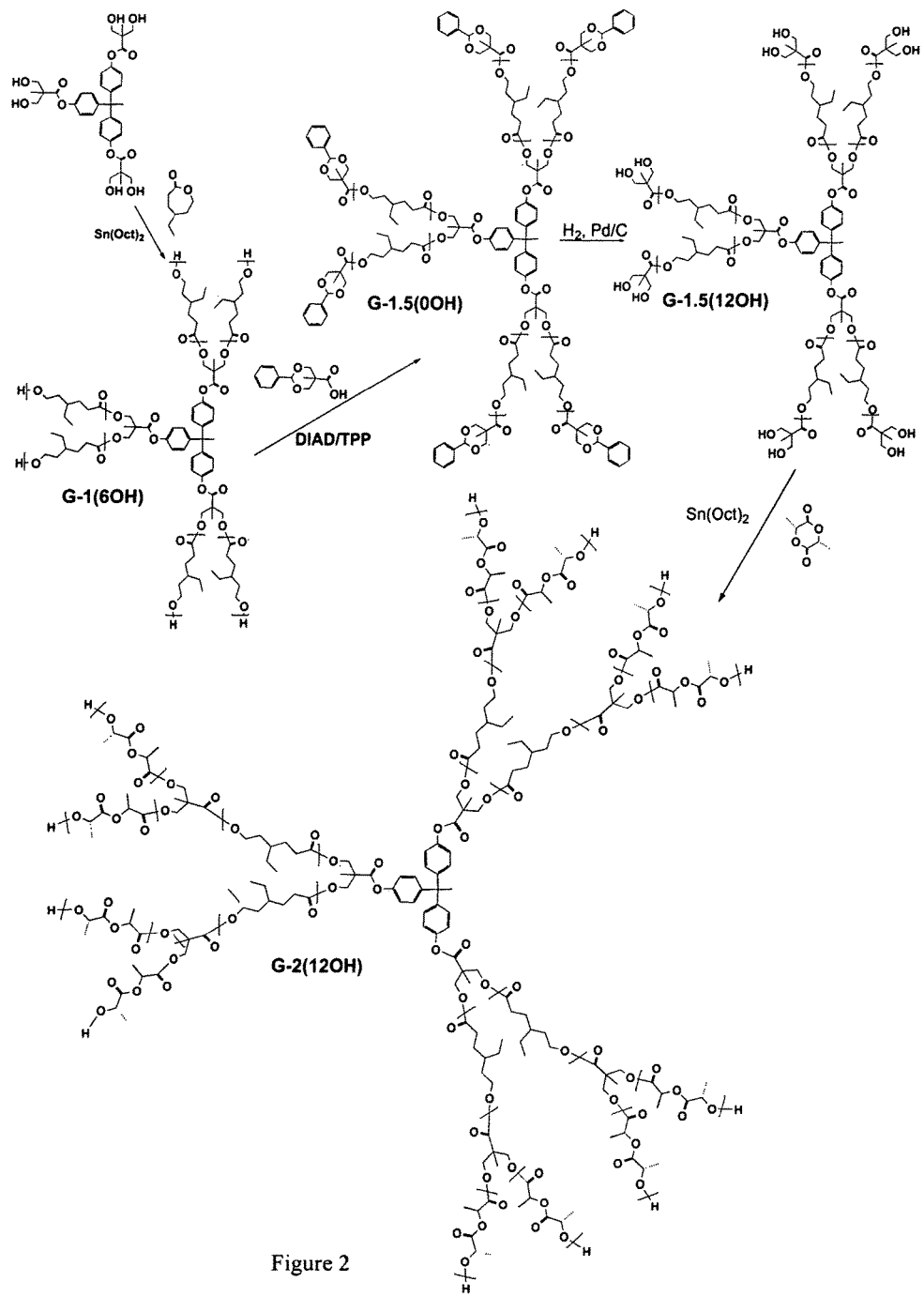
FIG. 2 shows the preparation of a branched substituted polycaprolactone block copolymer of an embodiment of the present invention.

In some embodiments, the substituted polycaprolactone can be a branched, block or random copolymer. Some examples of such branched, block or random copolymer of substituted caprolactone are shown in FIGS. 1 and 2.

The substituted polycaprolactone polymers can be readily synthesized according to established methodologies. For example, in some embodiments, substituted polycaprolcatone can be readily synthesized via ring-opening polymerization (ROP) of substituted caprolcatone. The polymerization can be carried out via a catalyst, e.g., an organic tin compound such as $Sn(Oct)_2$, and an initiator. An initiator is a molecule that initiates the ROP polymerization. Such an initiator generally includes an active terminal hydroxyl group(s) and can be generally shown as INT-OH. One such initiator can be, e.g., 2,2'-bis(hydroxymethyl)propionic acid (bis-MPA). A general scheme of forming a polycaprolactone is shown below in Scheme I, forming a substituted polycaprolactone comprising the general structure of Formula I:

Scheme I

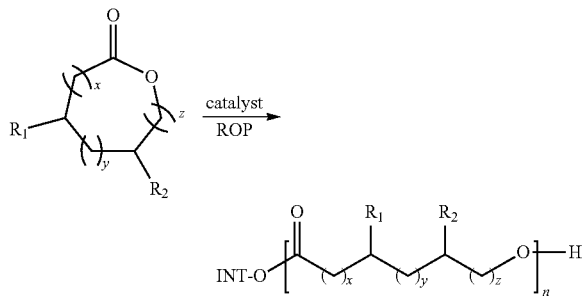

In Scheme I:
The catalyst can be any catalyst that catalyzes ring-opening polymerization of substituted caprolactone;
x, y, and z are independent integers having values ranging from 0-20, e.g., 0, 1, 2, 3, 4, 5, 6, 7, 8, 9, 10, 11, 12, 13, 14, 15, 16, 17, 18, 19 and 20;
n is an integer ranging from 1 to about 100,000, e.g., from about 5 to about 50,000, from about 10 to about 10,000, from about 100 to about 5,000, from about 500 to about 2,000 or about 1,000;
$R_1$ and $R_2$ are independently hydrogen or any of C1-C20 substituents. Some examples of $R_1$ and $R_2$ can be straight-chained or branch-chained alkyl groups, such as methyl, ethyl, propyl, isopropyl, n-butyl, or iso-butyl; cyclo alkyl or substituted cyclo alkyl groups, such as cyclohexyl or 1,4-dimethyl cyclohexyl; straight-chained or branch-chained alkoxy groups, such as methoxy, ethoxy, butoxy, or iso-butoxy; phenyl, phenoxy, aryl, or aryloxy, ketones, esters, olefins, ethers, unsaturations, thioethers, thioesters, amides, amines, thiols/mercaptans, phenols, other alcohols. In some embodiments. In some embodiments, $R_1$ and $R_2$ can independently include one or more

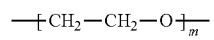

group where m is a positive integer ranging from 1 to 100, e.g., 2, 3, 4, 5, 6, 7, 8, 9, 10, 11, 12, 13, 14, 15, 16, 17, 18, 19, or 20. In some embodiments, $R_1$ and $R_2$ can independently include a heteroatom substituent(s) such as oxygen, halo atom(s) (F, Cl, Br or I), S, and N. In some embodiments, $R_1$ and $R_2$ can independently include one or more carbo substituent such as methyl, ethyl, or phenyl;
$R_1$ and $R_2$ cannot both be hydrogen; and
$R_1$, $R_2$, x, y, and z are selected such that the polymer generated in Scheme II is not a polylactic acid (PLA), polyglycolic acid (PGA), polyhydroxybutyric acid (PBH), polyhydroxyvaleric acid, valerolactone, caprolactone, dioxanone or a copolymer thereof.

In some embodiments, the caprolactone can be a dimer of an hydroxyacid. ROP of the dimer can generate a polymer as shown below in Scheme IA, forming a forming a substituted polycaprolactone comprising the general structure of Formula IA:

Scheme IA

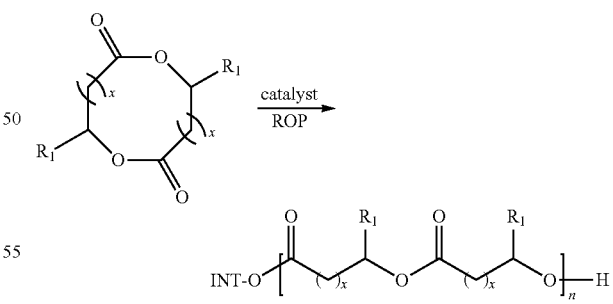

In Scheme IA:
The catalyst is as defined above;
x, y, and z are independent integers having values ranging from 0-20, e.g., 0, 1, 2, 3, 4, 5, 6, 7, 8, 9, 10, 11, 12, 13, 14, 15, 16, 17, 18, 19 and 20;
n is an integer ranging from 1 to about 100,000, e.g., from about 5 to about 50,000, from about 10 to about 10,000, from about 100 to about 5,000, from about 500 to about 2,000 or about 1,000;

The two $R_1$ groups are independently hydrogen or any of C1-C20 substituents. Some examples of $R_1$ can be straight-chained or branch-chained alkyl groups, such as methyl, ethyl, propyl, isopropyl, n-butyl, or iso-butyl; cyclo alkyl or substituted cyclo alkyl groups, such as cyclohexyl or 1,4-dimethyl cyclohexyl; straight-chained or branch-chained alkoxy groups, such as methoxy, ethoxy, butoxy, or iso-butoxy; phenyl, phenoxy, aryl, or aryloxy, aryloxy, ketones, esters, olefins, ethers, unsaturations, thioethers, thioesters, amides, amines, thiols/mercaptans, phenols, other alcohols. In some embodiments, In some embodiments, the two $R_1$ groups can independently include one or more

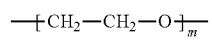

group where m is a positive integer ranging from 1 to 100, e.g., 2, 3, 4, 5, 6, 7, 8, 9, 10, 11, 12, 13, 14, 15, 16, 17, 18, 19, or 20. In some embodiments, the $R_1$ groups can independently include a heteroatom substituent(s) such as oxygen, halo atom(s) (F, Cl, Br or I), S, and N. In some embodiments, the $R_1$ groups can independently include one or more carbo substituent such as methyl, ethyl, or phenyl; The two $R_1$ cannot both be hydrogen; and The two $R_1$ groups and x are selected such that the polymer generated in Scheme II is not a polylactic acid (PLA), polyglycolic acid (PGA), polyhydroxybutyric acid (PBH), polyhydroxyvaleric acid, valerolactone, caprolactone, dioxanone or a copolymer thereof.

In some embodiments, substituted polycaprolactones for forming the coating or delivery vehicle described herein can be block copolymers comprising at least one block of a substituted polycaprolactone having a structure comprising the general formulae I or II, defined above. In some embodiments, the block copolymer can have two or more blocks of a substituted polycaprolactone having a structure comprising the general Formulae I or II, defined above. Where two or more blocks of different substituted polycaprolactones are included in the block copolymer, these different substituted polycaprolactones can have different molar ratios. The molar ratio for each of these blocks can range from about 0.01 to about 0.99. In some embodiments, the molar ratio each of these blocks can range from below 0.01 to above 0.99. Block copolymers comprising blocks of Formulae I or II can be readily prepared by one of ordinary skill in the art by coupling different blocks using standard coupling chemistry.

In some embodiments, the block copolymer of substituted polycaprolactone can be a branched block copolymer. The structure of the branched block copolymer depends on the core molecule, the initiator for ROP of a substituted caprolactone, and the polycaprolactone derived from the ROP of the substituted caprolactone. In some embodiments, the polycaprolactone can include a structure of Formulae I or II, defined above.

In some embodiments, to make a branched block copolymer, one can use an initiator that has at least three reactive functional groups, one of which being protected with a protective group. ROP of a substituted caprolactone with this initiator can generate a polycaprolactone with a structure having two blocks derived from the substituted caprolactone and the initiator unit in the middle of the two blocks. Deprotection of the protected group in the initiator unit generates a reactive functional group in the initiator unit of the polycaprolactone. Reaction of this polycaprolactone with a linker molecule having at least two reactive functional groups via the reactive functional group in the initiator unit generates a branched block copolymer comprising at least two polycaprolactone arms. Following this guidance, an ordinary artisan can generate branched block copolymer comprising different blocks of substituted polycaprolactone with different structure. Some examples of making branched block copolymer are shown in Scheme II (FIG. 1) and Scheme III (FIG. 2). In Scheme II and III, n and m are integers as defined above.

Scheme II shows that a substituted polycaprolactone block copolymer can be synthesized via an $AB_2$ type macromonomer(s) having three reactive groups. Poly(ε-caprolactone) and poly(L-lactide) $AB_2$ type macromonomers can be synthesized by the method according to Scheme I and Scheme IA (see also, Trollsas, M., et al., Macromolecules 1998, 31, 2756; Trollsas, M. Hedrick, J. L. Macromolecules 1998, 31, 4390). The protective group on the initiator can be readily removed by deprotection procedure (e.g., benzyl groups on the initiator were removed from the polymers by catalytic hydrogenation as previously reported). This transformation generates the requisite α-carboxylic-w-dihydroxy macromonomers.

In some embodiments, the copolymerization of the $AB_2$ macromonomers with three reactive groups can be performed in $CH_2Cl_2$ using dicyclohexylcarbodiimide (DCC) and 4-(dimethylamino)-pyridinum 4-toluenesulfonate (DPTS) as reagents (Scheme II, FIG. 1). For the most part, the compositions of the mixed $AB_2$ macromonomers in the copolymerization can be designed in such a way as to have the low-$T_g$, amorphous component as the continuous phase and the poly (ε-caprolactone) or poly(L-lactide) as the dispersed phase. The characteristics of the hyperbranched polycaprolactone copolymers are shown in Table 2 of Trollsas et al., Macromolecules, 32(15), 4917 (1999). In some embodiments, to reduce the content of possible un-reactive macromolecules, the macromonomers can be designed to be of moderate to low molecular weight so that un-reacted material after copolymerization may be readily removed during the copolymer precipitation in methanol.

In some embodiments, the substituted polycaprolactone can be a dendrimer-like star polymers (see Scheme III, FIG. 2). These block copolymers can be described by a radial geometry where the different generations or layers are comprised of high molecular weight polymer emanating from a central core. For mechanical property considerations, in some embodiments, the copolymer can be designed such that the interior of the radial copolymer be comprised of a low-$T_g$, amorphous component and the outer block (s) be comprised of a high-$T_g$ or semicrystalline component. For example, the polymers shown in FIG. 2 can be synthesized by polymerization initiated by the first-generation hexahydroxyl functional bis-MPA dendrimer in the presence of a catalytic amount of $Sn(Oct)_2$ using, e.g., bulk conditions according to procedures described in Trollsas, M.; Hedrick, J. L. *J. Am. Chem. Soc.* 1998, 120, 4644; Trollsas, M.; et al., *Angew. Chem.* 1998, 37, 3132; Atthoff, B.; et al., *Polym. Prepr. (ACS, Div. Polym. Chem.)* 1998, 39(2), 76; and Hedrick, J. L.; et al., *Macromolecules* 1998, 31, 8691 (Scheme 3, FIG. 2).

Other Polymers

A coating or a delivery vehicle can be formed of the substituted polycaprolactone alone or together with one or more other polymers. Representative polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactones not described above, poly(lactide-co-caprolactone), poly(glycolide-co-caprolactone), poly(dioxanone), poly(ortho esters), poly(trimethylene carbonate), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly (ether-esters) (e.g. PEO/PLA), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as HEMA, hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as collagen, chitosan, alginate, fibrin, fibrinogen, cellulose, starch, collagen, dextran, dextrin, fragments and derivatives of hyaluronic acid, heparin, fragments and derivatives of heparin, glycosamino glycan (GAG), GAG derivatives, polysaccharide, elastin, chitosan, alginate, or combinations thereof. In some embodiments, a coating or delivery vehicle described herein can exclude any one of the aforementioned polymers.

In some embodiments, a coating or delivery vehicle can further include a biobeneficial material. The biobeneficial material can be polymeric or non-polymeric. The biobeneficial material is preferably substantially non-toxic, non-antigenic and non-immunogenic. A biobeneficial material is one that enhances the biocompatibility of a device by being non-fouling, hemocompatible, actively non-thrombogenic, or anti-inflammatory, all without depending on the release of a pharmaceutically active agent.

Representative biobeneficial materials include, but are not limited to, polyethers such as poly(ethylene glycol), copoly (ether-esters) (e.g. PEO/PLA), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly (ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, PolyActive™, or combinations thereof. In some embodiments, a coating or delivery vehicle can exclude any one of the aforementioned polymers.

The term PolyActive™ refers to a block copolymer having flexible poly(ethylene glycol) and poly(butylene terephthalate) blocks (PEGT/PBT). PolyActive™ is intended to include AB, ABA, BAB copolymers having such segments of PEG and PBT (e.g., poly(ethylene glycol)-block-poly(butyleneterephthalate)-block poly(ethylene glycol) (PEG-PBT-PEG).

In a preferred embodiment, the biobeneficial material can be a polyether such as poly (ethylene glycol) (PEG) or polyalkylene oxide.

Bioactive Agents

In some embodiments, a coating or delivery vehicle described herein can include one or more bioactive agents. These bioactive agents can be any agent which is a therapeutic, prophylactic, or diagnostic agent. These agents can have anti-proliferative or anti-inflammatory properties or can have other properties such as antineoplastic, antiplatelet, anti-coagulant, anti-fibrin, antithrombotic, antimitotic, antibiotic, antiallergic, or antioxidant properties. Moreover, these agents can be cystostatic agents, agents that promote the healing of the endothelium, or agents that promote the attachment, migration and proliferation of endothelial cells while quenching smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules, which bind to complementary DNA to inhibit transcription, and ribozymes. Some other examples of bioactive agents include antibodies, receptor ligands, enzymes, adhesion peptides, blood clotting factors, inhibitors or clot dissolving agents, such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include ABT-578, 40-O-(3-hydroxy) propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include biolimus, tacrolimus, dexamethasone, clobetasol, corticosteroids or combinations thereof. Examples of such cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, and genetically engineered epithelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

In some embodiments, a coating or delivery vehicle described herein can specifically exclude any one or more of the above described agents.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by those of ordinary skill in the art.

Examples of Medical Devices

As used herein, a medical device may be any suitable medical substrate that can be implanted in a human or veterinary patient. Examples of such medical devices include self-expandable stents, balloon-expandable stents, stent-grafts, grafts (e.g., aortic grafts), heart valve prostheses, cerebrospinal fluid shunts, pacemaker electrodes, catheters, and endocardial leads (e.g., FINELINE and ENDOTAK, available from Abbott Vascular, Santa Clara, Calif.), anastomotic devices and connectors, orthopedic implants such as screws, spinal implants, and electro-stimulatory devices. The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable (e.g., bioabsorbable stent) or biostable polymers could also be used with the embodiments of the present invention.

In some embodiments, a device can be a drug delivery vehicle or drug delivery matrix.

Method of Use

Preferably, the medical device is a stent. The stent described herein is useful for a variety of medical procedures, including, by way of example, treatment of obstructions caused by tumors in bile ducts, esophagus, trachea/bronchi and other biological passageways. A stent having the above-described coating is particularly useful for treating diseased regions of blood vessels caused by lipid deposition, monocyte or macrophage infiltration, or dysfunctional endothelium or a combination thereof, or occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, carotid and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter that allows a stent in its collapsed configuration to be inserted into the passageway. The delivery catheter is inserted either percutaneously or by surgery into the femoral artery, radial artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

The implantable device can be implanted in any mammal, e.g., an animal or a human being. In some embodiments, the implantable device can be implanted in a patient in need of treatment by the implantable device. The treatment can be angioplasty or other type of treatments involving an implantable device.

A patient who receives the implantable device described herein can be male or female under normal body condition (e.g., normal weight) or abnormal body condition (e.g., underweight or overweight). The patient can be in any age, preferably, the patient is in an age ranging from about 40 to 70 years. An index for measuring the body condition of a patient is BMI (body mass index). A patient can have a BMI ranging from about 18 to about 30 or above.

The implantable device described herein can be used to treat or ameliorate a medical condition such as atherosclerosis, thrombosis, restenosis, hemorrhage, vascular dissection or perforation, vascular aneurysm, vulnerable plaque, chronic total occlusion, claudication, type-II diabetes, anastomotic proliferation for vein and artificial grafts, bile duct obstruction, ureter obstruction, tumor obstruction, or combinations thereof.

EXAMPLES

The embodiments of the present invention will be illustrated by the following prophetic examples. All parameters and data are not to be construed to unduly limit the scope of the embodiments of the invention.

Example 1. Coatings Formed of Highly Branched Polycaprolactone

Polymer Synthesis

Highly branched polycaprolactone polymer or dendrimers can be synthesized by polymerization of the caprolactone monomers below according to the description in Trollsas, M.; et al., Macromolecules 1999, 32, 4917. Some examples of monomers are 4-Methyl ε-caprolactone (1), 4-Ethyl ε-caprolactone (2), 4-Phenyl ε-caprolactone (3), and 3,5-Dimethyl ε-caprolactone (4). The macromonomers and dendrimer-like star block copolymers can be prepared according to literature procedures (Trollsas, M.; et al., Macromolecules 1997, 30, 8508; Trollsas, M.; Hedrick, J. L. *J. Am. Chem. Soc.* 1998, 120, 4644; Trollsas, M.; Atthoff, B.; Claesson, H.;
Hedrick, J. L. Macromolecules 1998, 31, 3439; Trollsas, M. Hedrick, J. L. Macromolecules 1998, 31, 4390).

Substituted polycaprolactone polymers listed in Tables 1 and 2, above, were synthesized and identified. Dendrimers shown in Scheme II (FIG. 1) and Scheme III (FIG. 2) were also synthesized and identified.

In the polymerization of Scheme III shown in FIG. 2, the initiator was synthesized by documented procedures (see, e.g., Ihre, H.; et al., *Macromolecules* 1998, 31, 4061). Ethyl-substituted ε-caprolactone was employed as the monomer for this first-generation star polymer containing six hydroxyl end groups and designated as G-1(6OH). The target degree of polymerization (DP) for each arm of the star polymer was 30, and the average DP measured by $^1$H NMR spectroscopy was 27. This translates into a total molecular weight of 23 000 g/mol. The polydispersity was found to be 1.27 by SEC. This value is somewhat higher than for the analogous poly(c-caprolactone) and may be a result of the longer reaction time (48 h). Nonetheless, the SEC chromatogram showed a monomodal distribution, and $^{13}$C NMR spectroscopy showed a quantitative initiation from all hydroxyl groups. G-1(6OH) was then functionalized with benzylidene protected bis-MPA, using diisopropyl azodicarboxylate (DIAD) and triphenylphosphine (TPP) in dry THE to generate G-1.5(0OH). The benzylidene was removed by catalytic hydrogenolysis to generate G-1.5(12OH), which contains 12 hydroxyl end groups. The $^1$H NMR spectra shows the two polymers and their intermediates. All the spectra show the major peaks that can be assigned to the repeating units of the monomer(s). The $^1$H NMR spectrum of G-1(6OH) shows one peak that can be assigned to the chain ends and a small peak from the initiator. Upon transformation of the chain ends from alcohols into esters, the chain end peak of the $^1$H NMR spectrum shifts, and five new peaks appear from the protected bis-MPA that can be assigned to the protected bis-MPA. Deprotection erases the peaks derived from the benzylidene part of the protected bis-MPA and shifts the peak for —CH$_2$ in bis-MPA) and the one for —CH$_3$ in bis-MPA. This deprotected polymer was then used as the macroinitiator (initiator) for the ROP of L-lactide to give the dendrimer-like star polymer G-2(12OH). The $^1$H NMR spectrum confirmed the formation of G-2 (12OH). $^1$H NMR spectroscopy also shows that the DP was 13 per arm (target 15), which translates to a total molecular weight of approximately 46 500 g/mol. The polydispersity was found to be 1.30 by SEC.

Forming a Coating

The substituted polycaprolactone synthesized or described above can be used to form coatings of the following prophetic constructs:

Construct A. As a Topcoat in a Drug Delivery Stent Coating for the Controlled Release of Paclitaxel from a Stent.

A first composition is prepared by mixing the following components:
(a) 2.0 mass % of poly(n-butyl methacrylate) (PBMA), and
(b) the balance, a 50/50 blend by weight of acetone and cyclohexanone.

The first composition is applied onto the surface of bare 12 mm small VISION™ stent (available from Abbott Vascular, Santa Clara, Calif.). Coating is sprayed and dried to form a primer layer. A spray coater is used having a 0.014 round nozzle maintained at about body temperature with a feed pressure 2.5 psi (0.17 atm) and an atomization pressure of about 15 psi (1.02 atm). Coating is applied at 20 µg per pass, in between which the stent is dried for 10 seconds in a flowing air stream at 50 C. Approximately 110 µg of wet coating is applied. The stents are baked at 50 C for one hour, yielding a primer layer composed of approximately 100 µg of PBMA.

A drug reservoir layer is applied onto the primer layer, using the same spraying technique, equipment, and formulation used for the applying the primer. A second composition is prepared by mixing the following components:
(a) 2.0 mass % of a substituted polycaprolactone polymer synthesized above,
(b) 0.67 mass % of paclitaxel, and
(c) the balance, a 50/50 blend of chloroform and 1,1,2-trichloroethane.

In this case approximately 220 µg of wet coating is applied, followed by drying, e.g., baking at 50 C for about one hour, yielding about 200 µg of drug-polymer reservoir layer. A polymer of the current invention is used as a topcoat layer. Starting with the same polymer of Formula III used in the drug reservoir, grafting of PEG is carried out using an amino-terminated mPEG of molecular weight of 3400 Daltons. Enough PEG derivative is conjugated so that the final composition is 20% by weight PEG. Using this composition, namely:
(a) 2.0 mass % of (IV) as described above, and
(b) the balance, a 50/50 blend of chloroform and 1,1,2-trichloroethane.

This composition can be applied onto the drug reservoir layer to form a topcoat layer. Using the same spraying technique and equipment used for applying the drug reservoir layer. Approximately 120 µg of wet topcoat is applied followed by baking at 50 C for one hour, yielding a 100 µg topcoat layer of Formula IV to act as a biobeneficial topcoat.

Construct B. As a Matrix in a Drug Delivery Stent Coating for the Controlled Release of Paclitaxel from a Stent.

A first composition is prepared by mixing the following components:
(a) 2.0 mass % of poly(n-butyl methacrylate) (PBMA), and
(b) the balance, a 50/50 blend by weight of acetone and cyclohexanone.

The first composition is applied onto the surface of bare 12 mm small VISION™ stent (available from Abbott Vascular, Santa Clara, Calif.). Coating is sprayed and dried to form a primer layer. A spray coater is used having a 0.014 round nozzle maintained at about body temperature with a feed pressure 2.5 psi (0.17 atm) and an atomization pressure of about 15 psi (1.02 atm). Coating is applied at 20 µg per pass, in between which the stent is dried for 10 seconds in a flowing air stream at 50 C. Approximately 110 µg of wet coating was applied. The stents are baked at 50 C for one hour, yielding a primer layer composed of approximately 100 µg of PBMA.

A drug reservoir layer is applied onto the primer layer, using the same spraying technique, equipment, and formulation used for the applying the primer. Starting with the same substituted polycaprolactone polymer, grafting of PEG is carried out using an amino-terminated mPEG of molecular weight of 550 Daltons. Enough PEG derivative is conjugated so that the final composition is 5% by weight PEG. Using this composition, namely:
(a) 2.0 mass % of (IV) as described above,
(b) 0.5 mass % of paclitaxel, and
(c) the balance, a 50/50 blend of chloroform and 1,1,2-trichloroethane.

This composition can be applied onto the primer layer to form a drug reservoir layer. Using the same spraying technique and equipment used for applying the drug reservoir layer. Approximately 280 µg of wet is applied followed by baking at 50° C. for one hour, yielding a 250 µg reservoir layer of a substituted polycaprolactone polymer to act as a reservoir polymer.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A coating on a medical device which comprises a substituted polycaprolactone;
    wherein the substituted polycaprolactone comprises units comprising a structure selected from

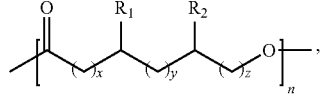

Formula I

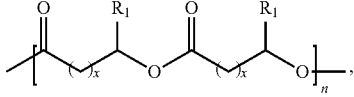

Formula II or
combinations thereof;
    wherein:
        x, y, and z are independent integers having values ranging from 0-20;
        n is an integer ranging from 1 to about 100,000;
        $R_1$ and $R_2$ are independently hydrogen, C1-C20 substituents, or C1-C20 substituents comprising one or more cyclohexyl, 1,4-dimethyl cyclohexyl, alkoxy, phenoxy, aryloxy, ketone, ester, thioether, thioester, amide, amine, thiol, or phenol groups;
        $R_1$ and $R_2$ cannot both be hydrogen;
        $R_1$, $R_2$, x, y, and z are selected such that the substituted polycaprolactone is not a polylactic acid (PLA), polyglycolic acid (PGA), polyhydroxybutyric acid (PBH), polyhydroxyvaleric acid, valerolactone, caprolactone, or dioxanone or where the substituted polycaprolactone is a copolymer, the structure of Formulae I or II are not both a polylactic acid (PLA), polyglycolic acid (PGA), polyhydroxybutyric acid (PBH), polyhydroxyvaleric acid, valerolactone, caprolactone, or dioxanone; and
        at least one $R_1$ or $R_2$ is a C1-C20 substituent comprising one or more cyclohexyl, 1,4-dimethyl cyclohexyl, alkoxy, phenoxy, aryloxy, ketone, ester, thioether, thioester, amide, amine, thiol, or phenol groups.

2. The coating of claim 1, wherein the substituted polycaprolactone comprises a branched structure.

3. The coating of claim 1, wherein the substituted polycaprolactone is a block copolymer.

4. The coating of claim 1, further comprising a bioactive agent.

5. The coating of claim 4, wherein the bioactive agent is paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, 40-O-(2-hydroxy)ethyl-rapamycin (everolimus), 40-O-(3-hydroxy)propyl-rapamycin, 40-O-[2-(2-hydroxy)ethoxy]

ethyl-rapamycin, 40-O-tetrazole-rapamycin, 40-epi-(N1-tetrazolyl)-rapamycin (ABT-578), γ-hiridun, clobetasol, mometasone, pimecrolimus, imatinib mesylate, midostaurin, or a combination thereof.

6. The coating of claim 5, wherein the bioactive agent is everolimus.

7. The coating of claim 1, wherein the medical device is a stent.

8. The coating of claim 7, wherein the medical device is a bioabsorbable stent.

9. A medical device comprising a copolymer according to claim 1.

* * * * *